United States Patent [19]
Hasnain et al.

[11] Patent Number: 5,965,393
[45] Date of Patent: Oct. 12, 1999

[54] METHOD FOR ENHANCING FOREIGN GENE EXPRESSION IN BACULOVIRUS EXPRESSION VECTOR SYSTEM

[75] Inventors: Seyed E. Hasnain; Betapudi Venkaiah; Saman Habib, all of New Delhi, India

[73] Assignee: National Institute of Immunology, New Delhi, India

[21] Appl. No.: 08/886,595

[22] Filed: Jul. 1, 1997

[51] Int. Cl.$^6$ .............................. C12N 15/86; C12N 5/10; C12P 21/00
[52] U.S. Cl. ...................... 435/69.1; 435/320.1; 435/325; 435/348; 435/456
[58] Field of Search ................................. 435/69.1, 172.1, 435/172.3, 320.1, 69.7, 69.8, 348, 325, 456

[56] References Cited

U.S. PATENT DOCUMENTS

| | | | |
|---|---|---|---|
| 4,745,051 | 5/1988 | Smith | 435/68 |
| 4,879,236 | 11/1989 | Smith | 435/235 |
| 5,169,784 | 12/1992 | Summers | 435/320.1 |
| 5,278,050 | 1/1994 | Summers | 435/69.1 |

OTHER PUBLICATIONS

Saman Habib, et al., "Bifunctionality of the AcMNPV Homologous Region Sequence . . ." DNA and Cell Biology, vol. 15 No. 9 1996, Mary Ann Liebert Inc. pp. 737–747.

Margot Pearson, et al., "The Autographa californica Baculovirus Genome: . . ." Science vol. 257, Sep. 4, 1992, pp. 1382–1384.

Udayan Chatterji, et al., "A recombination–efficient baculovirus vector for . . ." Gene, 171 (1996) 209–213.

Old, R.W. et al., "Principles of Gene Manipulation", Studies in Microbiology, 5th Ed., pp. 335, 337.

Kool, M. et al., "Location of Two Putative Origins of DNA Replication of Autographa . . ." Virology, 192, pp. 94–101 (1993).

Guarino, Linda A. et al., "Complete Sequence and Enhancer Function . . ." Journal of Virology, vol. 60, No. 1 Oct. 1986, pp. 224–229.

*Primary Examiner*—David Guzo
*Attorney, Agent, or Firm*—Ladas & Parry

[57] ABSTRACT

The baculovirus homologous region (hr1) sequence has been disclosed as a transcriptional enhancer of foreign gene expression. An additional copy of the hr1 element contained within a recombinant baculovirus has been demonstrated to be capable of further enhancing expression of foreign genes placed under the transcriptional control of a promoter such as the baculovirus polyhedrin and/or Drosophila hsp70 promoter. The recombinant baculovirus is stable for up to 30 passages. This invention can be employed to generate recombinant expression vector plasmids and recombinant baculoviruses that can be used to produce increased levels of recombinant protein products of therapeutic, biomedical or basic science research interest.

51 Claims, 14 Drawing Sheets

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH:       20 base pairs
      (B) TYPE:         Nucleotide
      (C) STRANDEDNESS: Single
      (D) TOPOLOGY:     Linear (ix) SEQUENCE DESCRIPTION:  SEQ ID NO: 1:

AAGAATGTAA CACAAAGGAA                                           20

(2) INFORMATION FOR SEQ ID NO:2:

(i) SEQUENCE CHARACTERISTICS:
      (A) LENGTH:       18 base pairs
      (B) TYPE:         Nucleotide
      (C) STRANDEDNESS: Single
      (D) TOPOLOGY:     Linear (xi) SEQUENCE DESCRIPTION:  SEQ ID NO: 2:

TGTTTTACTA TCTGTTCT                                             18

(2) INFORMATION FOR SEQ ID NO:3:

(i) SEQUENCE CHARACTERISTICS:
      (A) LENGTH:       18 base pairs
      (B) TYPE:         Nucleotide
      (C) STRANDEDNESS: Single
      (D) TOPOLOGY:     Linear (xi) SEQUENCE DESCRIPTION:  SEQ ID NO: 3:

GTTGTCGATA AAACATTC                                             18

(2) INFORMATION FOR SEQ ID NO:4:

(i) SEQUENCE CHARACTERISTICS:
      (A) LENGTH:       21 base pairs
      (B) TYPE:         Nucleotide
      (C) STRANDEDNESS: Single
      (D) TOPOLOGY:     Linear (xi) SEQUENCE DESCRIPTION: SEQ ID NO: 4:

CGATGTTAAA TATGTCCAAG C                                         21

METHOD FOR ENHANCING FOREIGN GENE EXPRESSION IN BACULOVIRUS EXPRESSION VECTOR SYSTEM

FIELD OF THE INVENTION

This invention provides a way to improve the efficiency of the baculovirus expression vector system (BEVS) to produce higher levels of expression of foreign genes. This invention describes a novel approach that utilizes an enhancer sequence for the development of an efficient baculovirus expression vector plasmid and a recombinant baculovirus constructed using this expression vector plasmid. A recombinant baculovirus constructed using an expression vector plasmid is a viral expression vector. This invention also includes cells that have been transformed by the expression vector plasmid or by the baculovirus expression vector. Following the strategy given below a recombinant baculovirus can be constructed which results in a higher yield of the desired protein product. A higher yield of the desired protein product can also be obtained when the expression vector plasmid is used to transform cells.

BACKGROUND OF THE INVENTION

The baculovirus expression vector system (BEVS) has gained acceptance as the system of choice for the expression of foreign genes of both prokaryotic and eukaryotic origin (V. A. Luckow & M. D. Summers, Biotechnology, Vol. 6, 47–55, 1988). This expression system is one of the easiest and safest eukaryotic systems for recombinant protein production. A number of genes of both prokaryotic and eukaryotic origin have been expressed using this system. BEVS primarily utilizes the Autographa californica multiple nuclear polyhedrosis virus (AcMNPV), the prototype baculovirus which infects Lepidopteran insects. On the basis of their temporal activation profile in the infected insect host, baculovirus genes are classified as early, late and very late (D. R. O'Reilly, et al., In: Baculovirus Expression Vectors: A Laboratory Manual, New York: W H Freeman and Co, 1992). For the purpose of foreign gene expression, promoters that drive the transcription of late and very late genes are most commonly used. These include the late cor promoter and the very late p10 and polyhedrin gene promoters.

The polyhedrin promoter, utilized extensively in BEVS is temporally regulated and hyperactive (V. S. Luckow & M. D. Summers, Biotechnology, Vol. 6, 47–55, 1988: M. D. Summers, Curr. Commun. in Molec. Biol., Cold Spring Harbor Press. Cold Spring Harbor, N.Y. 1987; M. D. Summers & G. E. Smith, TAES Bulletin No. 1555, 1988; Smith and Summers, U.S. Pat. Nos. 4,745,051 and 4,040,367; M. D. Summers et al. 5,169,784; Webb & Summers, vol. 2, Technique—A Journal of Methods in Cell and Molec. Biology, 173–188, 1990).

There are eight interspersed homologous regions (hrs) that vary in size from 30 to 800 bp distributed in the double-stranded, covalently closed baculovirus DNA genome (M. A. Cochran & P. Faulkner, Vol. 45, J. Virology, 961–970,1983; Kool, et al. Vol. 74, J. General Virology, 2661–2668, 1993; S.M. Rodems & P. D. lriesen, Vol. 69, J. Virology, 5365–5378, 1995). These are designated as hrl, hrla, hr2, hr3, hr4a, hr4b, hr4c and hr5. The sequence homology between these regions is due to the presence of conserved 30 bp palindromic repeats (L. A. Guarino et al. Vol. 60, J. Virology, 224–229, 1986; L. A. Guarino & M. D. Summers. Vol. 60, J. Virology 215–223, 1986; A. Liu et al. Vol. 67, J. General Virology, 2565–2570, 1986). The homologous region sequences are capable of functioning as origins of replication (ori) (M. Pearson, et al. Vol. 257, Science, 1382–1384, 1992; M. Kool et al. Vol. 192, Virology, 94–101, 1993; M. Kool et al. Vol. 198, Virology, 680–689, 1994; C.H. Ahrens, et al. Baculovirus DNA replication, DePamphilis, M. (ed.) In: DNA replication in eukaryotes, 1995; M. Kool, et al. Vol. 76, J. General Virology, 2103–2118, 1995; D. J. Leisy & G. F. Rohrmann, Vol. 196, Virology, 722–730, 1993) as well as enhancers of some viral genes (S. M. Rodems & P. D. Friesen, Vol. 69, J. Virology, 5365–5378, 1995; L. A. Guarino, et al. Vol. 60, J. Virology, 224–229, 1986; L. A. Guarino & M. D. Summers, Vol. 60, J. Virology, 215–223, 1986; D. D. Carson et al. Vol. 65, J. Virology, 945–951, 1991; A. Lu & E. B. Carstens, Vol. 195, Virology, 710–718, 1993; M. S. Nissen, & P. D. Friesen, Vol. 63, J. Virology, 493–503, 1989; S. M. Rodems & P. D. Friesen, Vol. 67, J. Virology, 5776–5785, 1993; L. A. Guarino & W. Dong, vol 65, J. Virology, 3676–3680, 1991; L. A. Guarino, & W. Dong, Vol. 200, Virology, 328–335, 1994). The hr5, in particular, has been demonstrated to function as an enhancer of the delayed early 39K gene (S. M. Rodems & P. D. Friesen. Vol. 69, J. Virology, 5365–5378, 1995). The applicants previously demonstrated that the hr1 homologous region sequence, located about 3.7 kb upstream to the polyhedrin promoter in the wild type AcMNPV genome, enhances transcription from the polyhedrin promoter in a position- and orientation-independent manner in transient expression assays (S. Habib et al. Vol. 15, DNA Cell Biology, 737–747, 1996). Enhancement of expression was demonstrated to be a direct result of enhanced transcription from the promoter and was independent of the ori function of hr1.

The property of viral enhancers has not been exploited in the baculovirus expression vector system. Specifically, hr1 has not been exploited in baculovirus expression plasmids or baculovirus expression vectors for enhanced foreign gene expression in insect cells.

It is an object of this invention to produce expression vector plasmids that can be used to construct viral expression vectors or that can be used to tra isect cells to enhance the expression of foreign genes in insect cells.

It is an object of this invention to produce a baculovirus expression vector to enhance the expression of foreign genes in insect cells.

It is a further object of this invention to construct a recombinant baculovirus expression plasmid that can be used to construct a baculovirus expression vector which can be used to increase the yield of the desired protein product or protein products.

It is another object of this invention to construct a recombinant baculovirus enhancer of foreign gene expression driven by the baculovirus polyhedrin promoter.

It is yet another object of the invention to construct a recombinant baculovirus enhancer of foreign gene expression driven by the Drosophila hsp 70 promoter.

A still further object of the invention is to construct a recombinant baculovirus expression vector comprising hrl as a transcriptional enhancer of foreign gene expression driven by the baculovirus polyhedrin gene promoter.

Yet another object of this invention is an approach for the construction of a recombinant baculovirus expression vector comprising hrl as a transcriptional enhancer of foreign gene expression driven by the Drosophila hsp 70 promoter.

Still another object of this invention is an approach for the construction of a recombinant baculovirus expression vector comprising hrl as a transcriptional enhancer of the expression of one or more foreign genes driven by the baculovirus polyhedrin gene promoter and/or Drosophila hsp 70 promoter.

Yet another object of this invention is an approach for the construction of a recombinant baculovirus expression vector comprising two hr1 sequences as transcriptional enhancers of the expression of one or more foreign genes under the control of multiple promoters such as two polyhedrin promoters, two Drosophila hsp 70 promoters or a polyhedrin promoter and a Drosphila hsp 70 promoter.

SUMMARY OF THE INVENTION

The present invention provides a method for creating recombinant baculoviruses for higher level of expression of foreign genes of both prokaryotic and eukaryotic origin in the baculovirus expression vector system (BEVS). The term foreign gene is known and understood by those of skill in the art and this knowledge and understanding is incorporated herein. A foreign gene includes but is not limited to a gene that this inserted into a plasmid, vector or recombinant virus of this invention. The foreign gene may be a gene that is not normally present in wild-type baculovirus. The enhancer function of AcMNPV baculovirus homologous region 1 (hr1) sequence has been utilized in this invention. By employing a baculovirus expression vector plasmid having a copy of the hr1 enhancer element placed downstream to one or more foreign gene cloning sites, a recombinant virus expression vector carrying an additional copy of the hr1 sequence was constructed. By using this recombinant virus expression vector carrying an additional copy of the hr1 sequence the expression levels of one or more foreign genes of biomedical, therapeutic or basic scientific interest placed under the transcriptional control of one or more homologous promoters (for example, polyhedrin promoter) or one or more heterologous promoters (for example, Drosophila hsp70 promoter) or one or more homologous promoters and one or more heterologous promoters or one or more polyhedrin promoters and one or more Drosophila hsp 70 promoters is elevated. The foreign gene expression may be enhanced 40–100 fold. If the expression vector plasmid is used directly to transfect the insect cell wild type baculovirus also has to be present in the cell to provide the necessary helper function required to activate transcription from the promoter present in the expression vector plasmid. In this method, foreign gene expression may be enhanced 12–18 fold. In a viral expression vector containing two hr1 sequences such sequence can drive transcription from at least one homologous promoter such as the polyhedrin promoter, at least one heterologous promoter such as Drosophila hsp 70 promoter or at least one homologous and heterologous promoter such as the polyhedrin promoter and the Drosophila hsp 70 promoter. This viral expression vector can also be used to simultaneously produce higher expression levels of two or more different proteins. The utilization of the baculovirus hr1 as an enhancer element per se as well as the use of an additional hr1 sequence for greatly enhanced foreign gene expression are hallmarks of this invention. The terms "recombinant baculovirus", "virus expression vector" and "recombinant baculovirus vector" are used interchangeably and synonomously herein.

DETAILED DESCRIPTION OF THE INVENTION

Applicants have demonstrated that hr1 is capable of increasing transcription from the viral polyhedrin gene promoter in an enhancer-like manner and that the enhancement is independent of its putative role as an ori sequence. (See S. Habib et al. Vol. 15, DNA Cell Biology, p.737–747). The following description of the invention refers to use of foreign genes coding for luciferase and β-galactosidase and the enhancement of luciferase and β-galactosidase produced from these genes. However, these are illustrative only and the scope of the invention is not limited thereto. hr1 mediated enhanced expression described herein can be used to enhance expression of any other foreign gene of biomedical, therapeutic or basic scientific interest.

Figure 10:
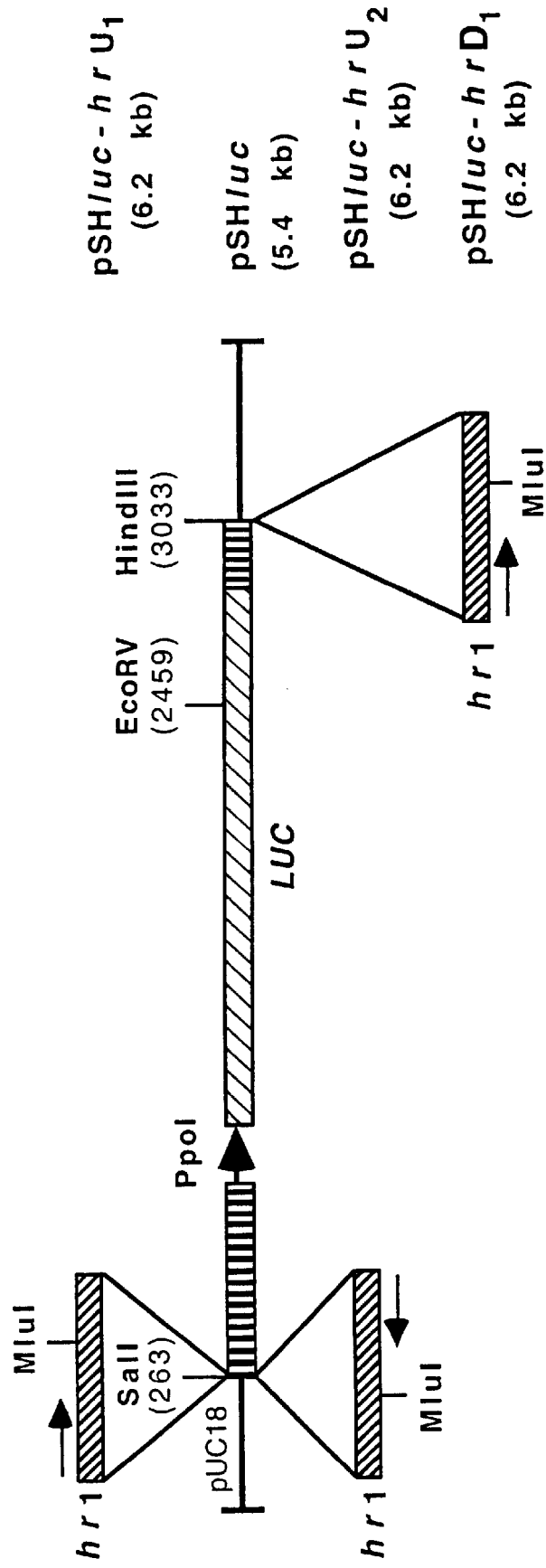
FIG. 10. Linear map of plasmid constructs used for transfection. The stippled box represents the luc gene, the filled arrow is the polyhedrin gene promoter, and the filled boxes indicate viral sequences immediately upstream to the polyhedrin promoter and downstream to the luc gene. The hatched box represents hr1 cloned 730 bp upstream and 80 bp downstream of the promoter-reporter cassette.

As disclosed in S. Habib et al. Vol. 15, DNA Cell Biology, p. 737–747, the 746-bp hr1 sequence, was cloned in the SalI site of pSHluc, thereby placing it 730 bp upstream of the promoter in the constructs of pSHluc-hrU$_1$ and pSHluc-hrU$_2$ in an orientation similar to or opposite of its normal orientation in the viral genome, respectively. hr1 was also cloned, downstream to the promoter-reporter cassette, as a SmaI-Hind III fragment in pSHluc to generate the construct pSHluc-hrD1 (FIG. 10).

Figure 11:
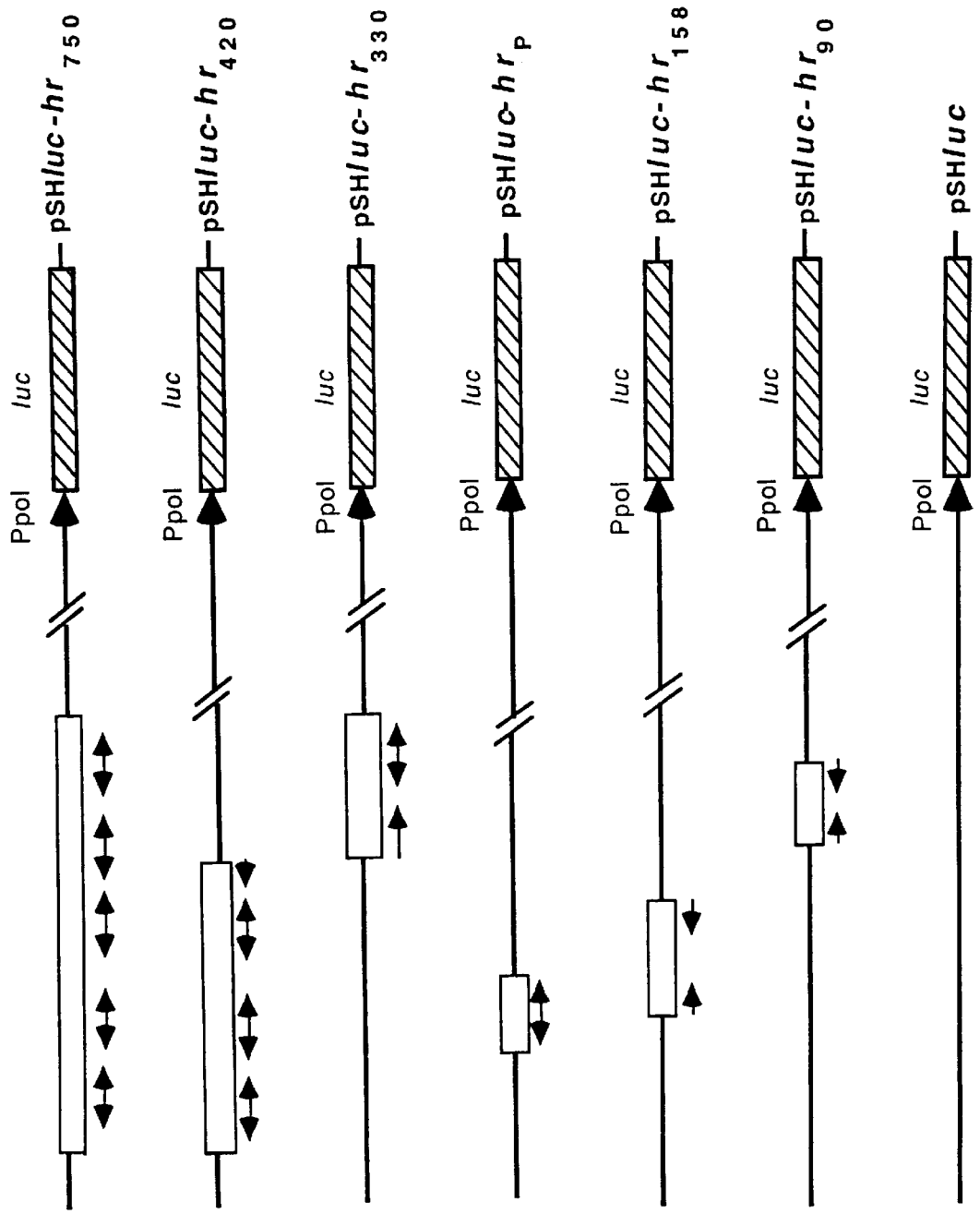
FIG. 11. Map of the plasmid constructs carrying different components of hr1.

The 420-bp and 330-bp Sal I-Mlu I fragments derived from pSHhr1 were cloned in the Sal I site of pSHluc to generate the plasmids pSHluc-hr420 and pSHluc-hr330. hr1 was digested with Eco RI to generate 158-bp and 90 bp fragments containing intermediate sequences flanked by half-palindromes and cloned in the Eco RI site of pUC18 in the constructs pUChr158 and pUChr90, respectively. The Sal I-Hind III fragment from pAcluc carrying the promoter-reporter cassette was then cloned into these plasmids to give the constructs pSHluc-hr158 and pSHluc-hr90 (FIG. 11).

The effect of hr1 on expression of the luc gene cloned under the polyhedrin promoter was measured in transient expression assays-a strategy used earlier for determining hr functions (Guarino and Dong, 1994). luc expression from AcMNPV infected Spodoptera frugiperda (Sf9) cells transiently transfected with one of the following plasmids pSHluc-hrU1, pSHluc-hrU2 or pSHluc-hrD1 carrying the hr1 sequence was compared with expression from cells transfected with pSHluc. The presence of hr1 in the same orientation relative to the polyhedrin gene promoter as in the viral genome (pSHluc-hrU1) resulted in an 11-fold increase in luciferase expression over the control plasmid pSHluc, whereas hr1 in the same position, but in an opposite orientation (pSHluc-hrU2), caused seven fold increase in expression. Expression was enhanced about 10-fold with hr1 present downstream to the reporter in pSHluc-hrD1.

The observation that hr1 can also exert its influence in a distance-independent manner, even when placed 6 kb upstream to the polyhedrin promoter (Venkaiah et al., unpublished observation) qualifies the categorization of the hr1 sequence as a classical enhancer element.

On the basis of their previous results on the enhancer function of hr1 in transient expression assays (S. Habib et al. Vol. 15, DNA Cell Biology, 737–747, 1996), the applicants extended the study to address the possibility of utilitizing this sequence for further improvement of the baculovirus expression vector system.

Figures 1, 1A:
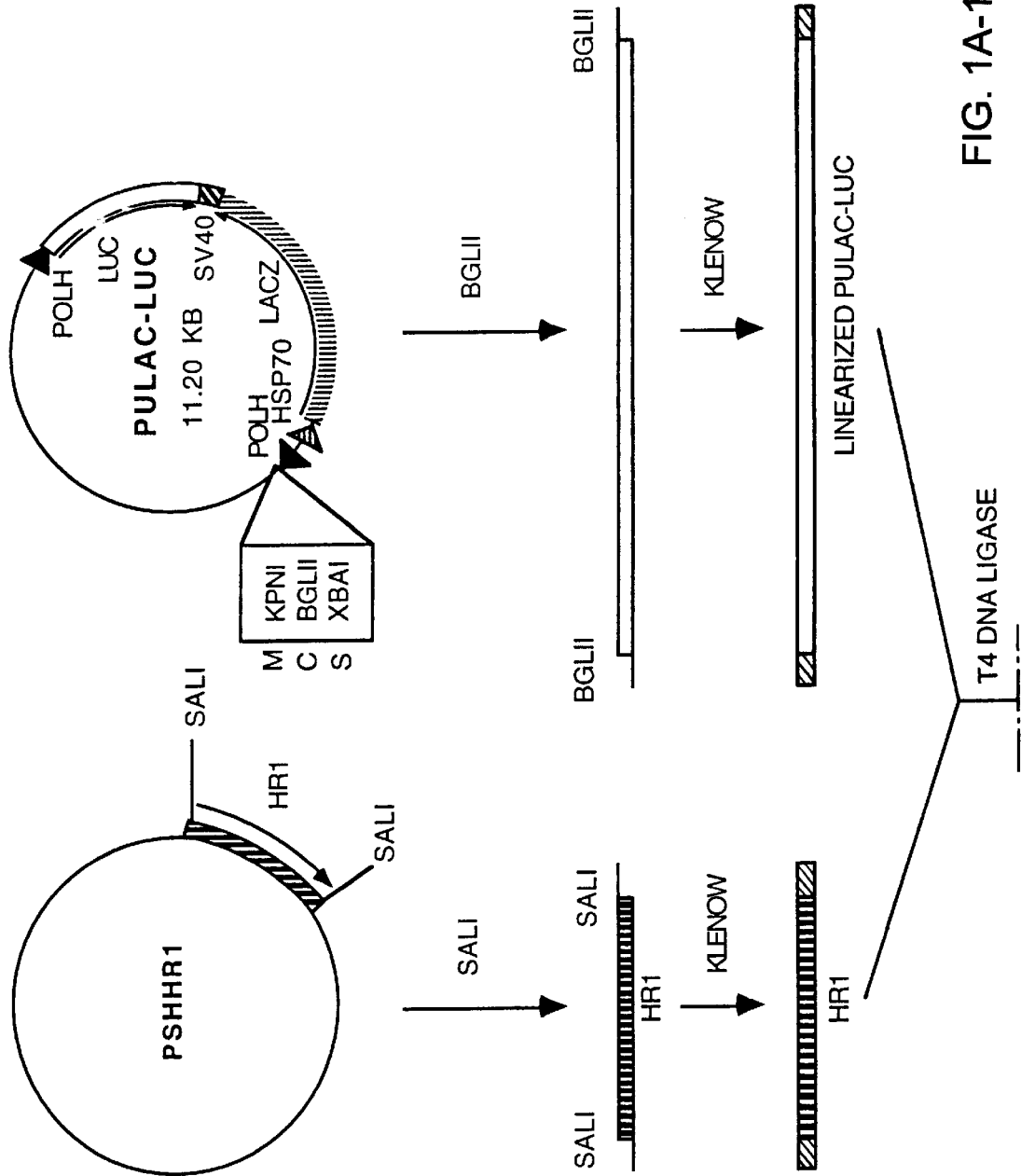
FIG. 1a. Illustrates the cloning strategy for the construction of the transfer vector plasmid pBVlac-luc-hr1 that carries a copy of hr1 sequence element for enhanced expression of reporter genes luc and lacZ under the transcriptional control of the viral polyhedrin gene promoter and Drosophila hsp70 promoter, respectively.
Figures 1, 1A, 2:
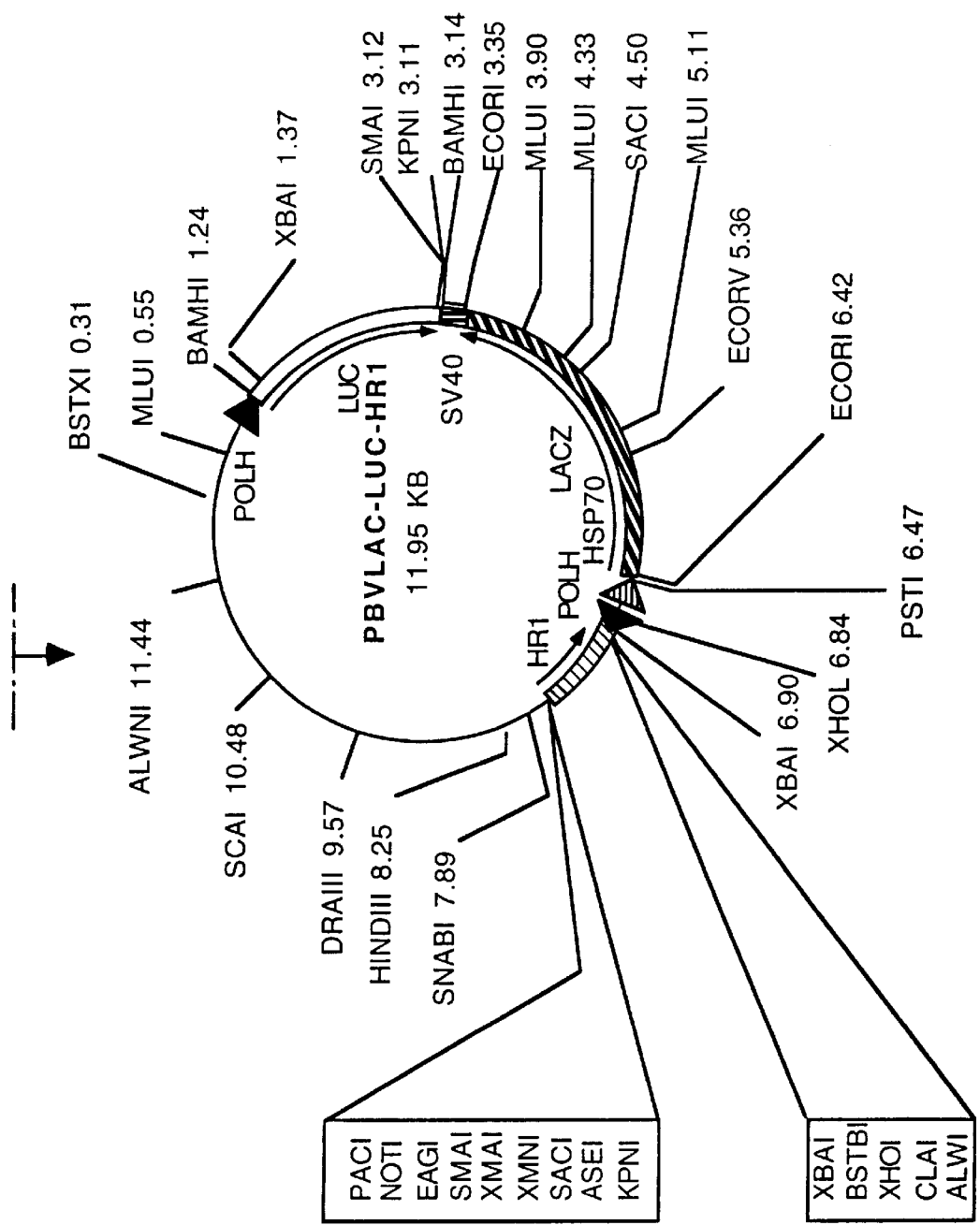
FIG. 2. Depicts the enhancement (15–18 fold) of luciferase reporter expression under the control of the baculovirus polyhedrin promoter in the presence of hr1 in transient expression assays. Mean values of the experiments carried out in duplicates are shown.
Figures 1, 1B:
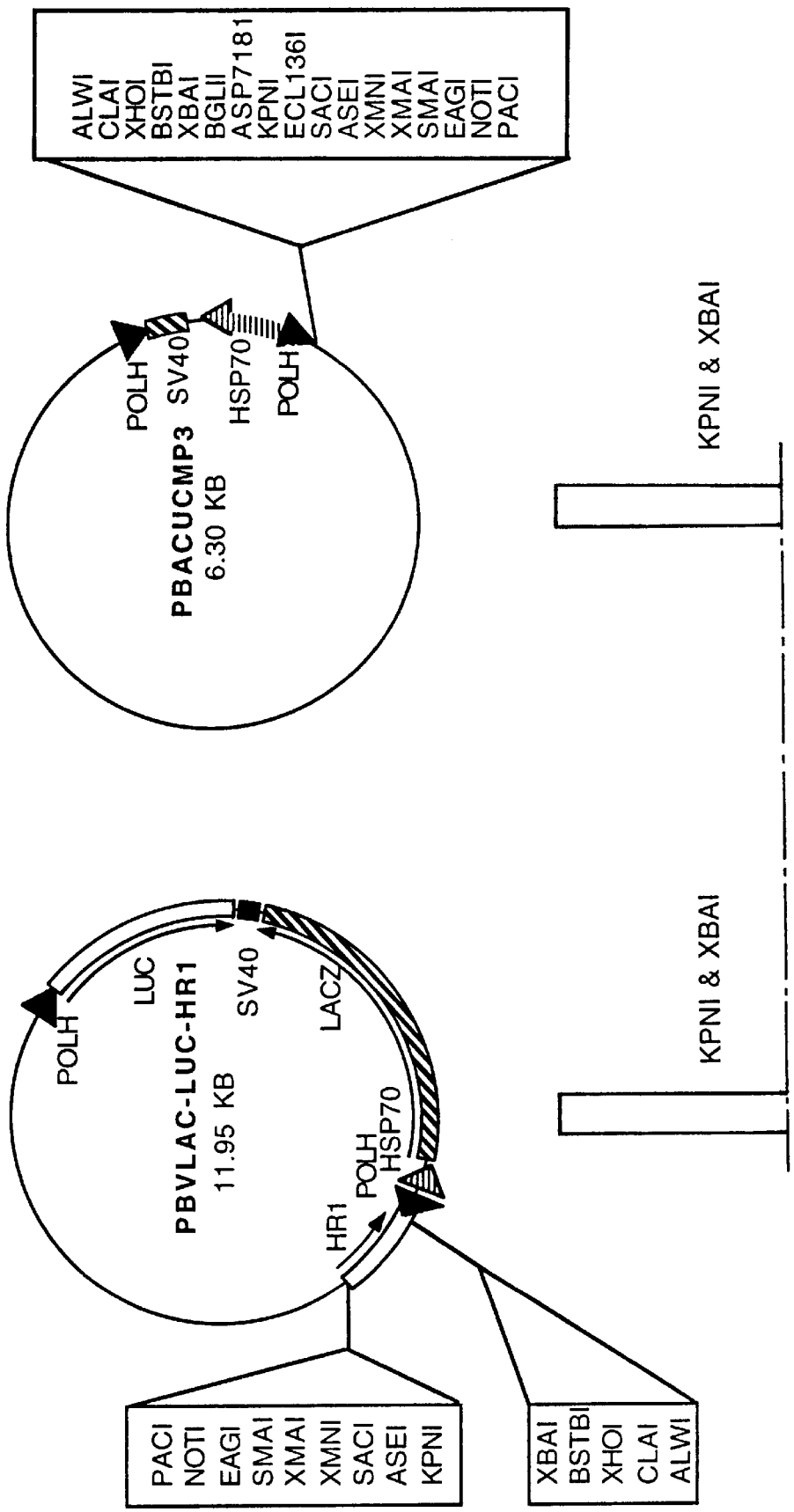
FIG. 1b. The construction of the transfer vector plasmid pBVhr1 lacking any reporter gene for cloning different foreign genes under the transcriptional control of the polyhedrin promoter and the hsp70 promoter is shown.
Figures 1, 1B, 2:
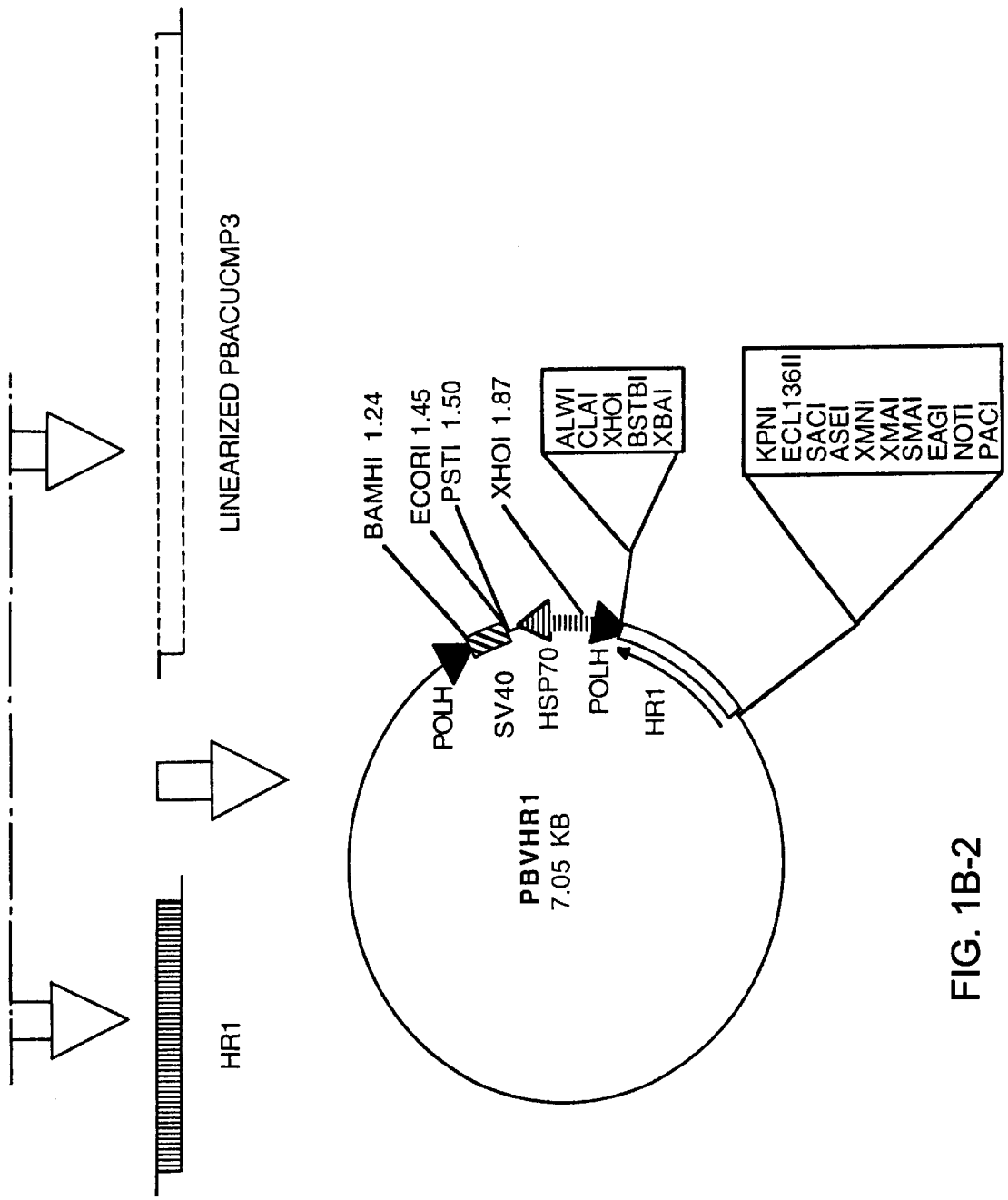
Figure 2:
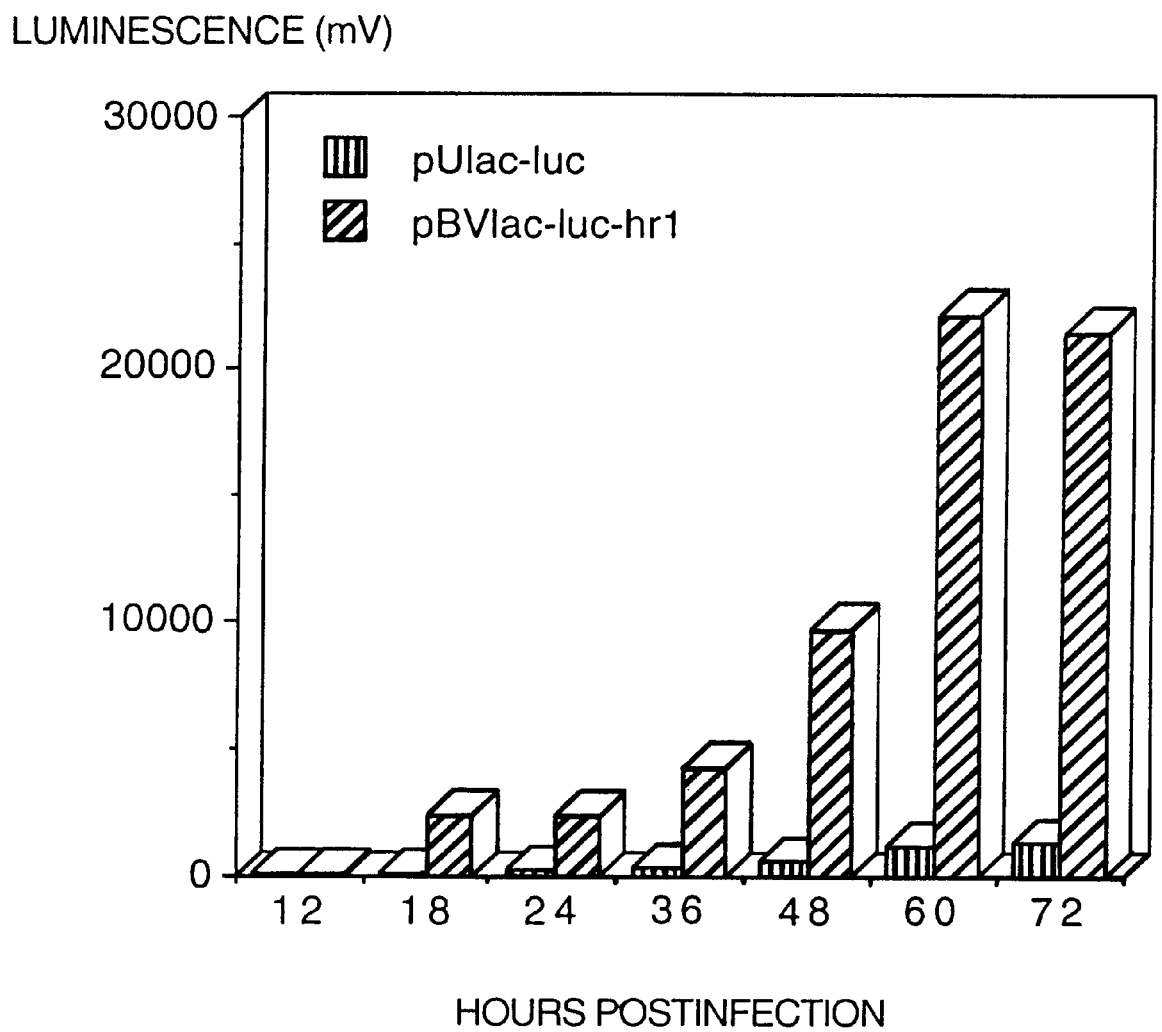
Figure 3:
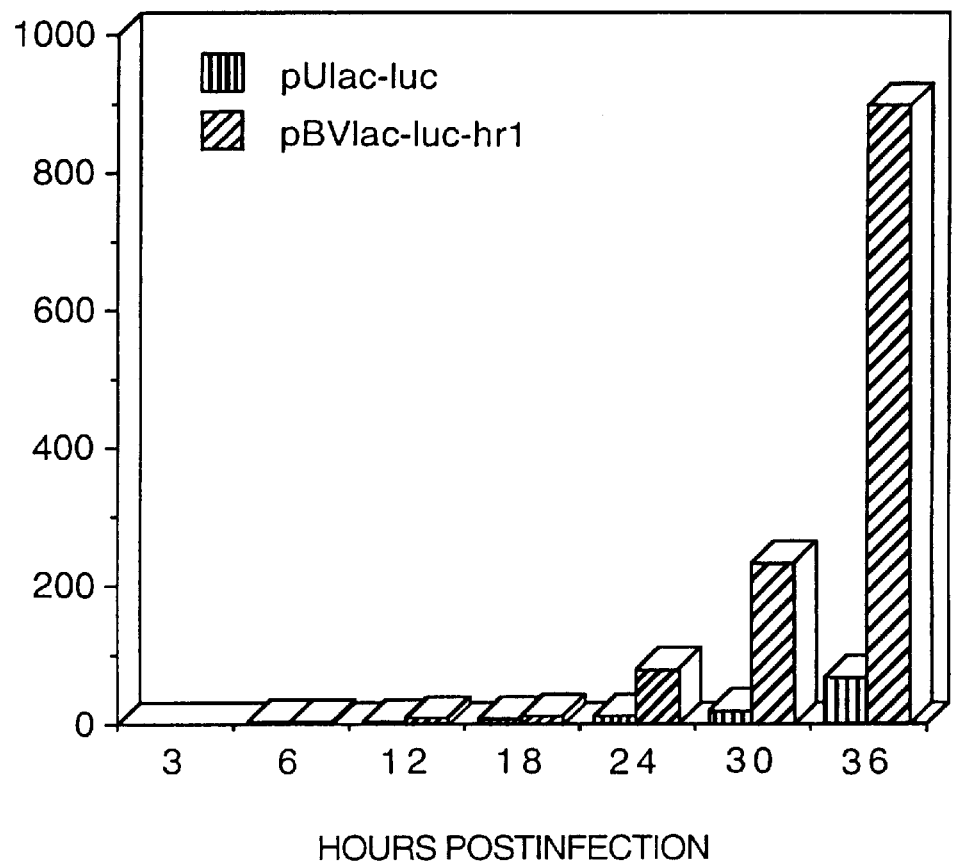
FIG. 3. Illustrates the enhancement (8–12 fold) of β-galactosidase reporter expression under the control of the Drosophila hsp70 promoter in the presence of hr1 in transient expression assays. Mean values of the experiments carried out in duplicates are shown.

A multiple expression vector plasmid (ptJlac-luc) carrying two reporter genes under a homologous (polyhedrin) and a heterologous (Drosophila hsp 70) promoter was modified to include a copy of the hr1 element (pBVlac-luc-hr1) (See FIG. 1a). The applicants earlier constructed the plasmid pUlac-luc (U. Chatterji et al, Vol. 171, Gene, 209–213, 1996) which carries two copies of the polyhedrin gene promoters (polh) and a single copy of the Drosophila hsp70 promoters(hsp70). The reporter genes luc (luciferase) and lacZ (Escherichia coli β-galactosidase) are cloned under the transcriptional control of the polh and hsp70 promoters, respectively. The hr1 sequence excised as 0.752 kb Sal 1 fragment from pSHhr1 (S. Habib et al. Vol. 15, DNA Cell Biology, 737–747, 1996) was cloned into the unique BglII site of pUlac-luc, to construct the recombinant expression vector plasmid pBVlac-luc-hr1 (FIG. 1a). The construction of the transfer vector plasmid pBVhr1 for cloning one or more foreign genes of interest is shown in FIG. 1b. In this construct, the orientation of hr1 with respect to the hsp70 promoter is same as the normal orientation of hr1 with respect to the polyhedrin promoter in the wild-type viral genome. pBVlac-luc-hr1 has the luc gene cloned under polh and the lacZ gene under hsp70. An SV40 terminator between the upstream polh and the hsp70 promotes termination of transcription of the reporter genes cloned under these promoters, at this site. The applicants carried out transient expression assays to study the effect of the hr1 element on reporter gene expression directed by the polh promoter as well as the heterologous hsp70 promoter. The cell lines Sf9 and Sf21 derived from Spodoptera frugiperda each maintained at 27° C. in TNM-FH medium (W. F. Hink, Vol. 226, Nature, 466–467, 1970) supplemented with 10% fetal calf serum (D. R. O'Reilly, et al. Baculovirus expression vectors: A Laboratory Manual, New York: W H Freeman and Co, 1992) were used for transient expression studies. Cells infected with either wild type or recombinant baculoviruses or transfected with expression vector plasmid DNAs in the presence of wild type baculovirus were harvested at different time hours post infection. β-Galactosidase enzyme expression levels were monitored by a colorimetric assay using the substrate p-nitrophenyl-β-galactopyranoside (ONPG) (J. H. Miller, A Short Course in Bacterial Genetics. A Laboratory Manual and Handbook for Escherichia coli and related bacteria. CSHL Press, Cold Spring Harbor, N.Y. 1992; G. D. Pennock et al. Vol. 4, Molecular Cell Biology, 399–406, 1984). The assay for luciferase activity was carried out as described by S. Habib et al. Vol. 15, DNA Cell Biology 737–747, 1996. A clear enhancement of reporter gene expression, in the presence of hr1, was observed for both the promoters. The level of enhancement of luciferase under the control of the polh promoter increased as infection progressed with maximum enhancement of 15 to 18-fold being attained at 60 h.p.i. (hours post-infection) (FIG. 2). About 12-fold enhancement of β-galactosidase activity in the presence of hr1 was seen at 36 h.p.i. (FIG. 3). This data demonstrates that hr1 is capable of enhancing expression of foreign genes from both homologous and heterologous promoters.

Figure 4:
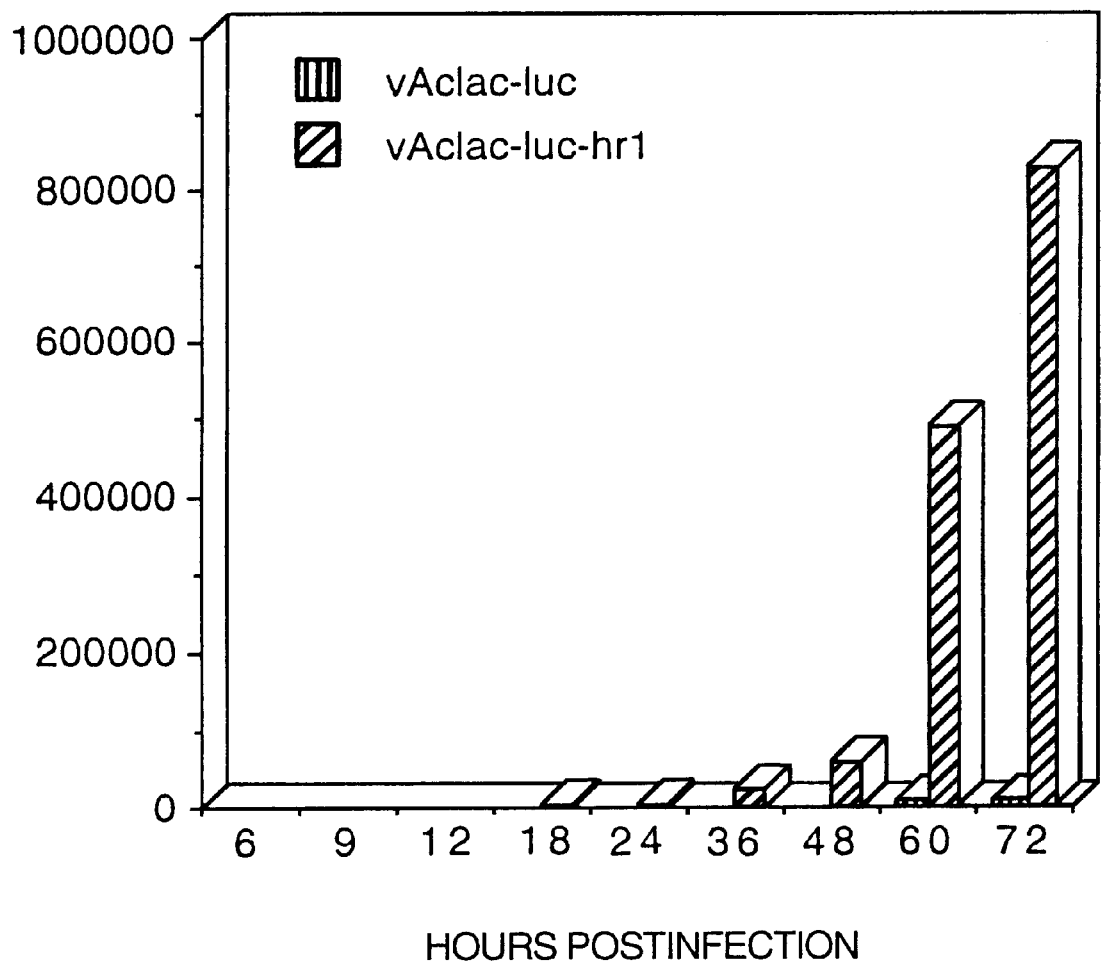
FIG. 4. Illustrates the enhancement (90–100 fold) of luciferase reporter expression in insect cells infected with the recombinant baculovirus expression vector carrying an additional copy of hr1 (vAclac-luc hr1). Mean values of the experiments carried out in duplicates are shown.
Figure 5:
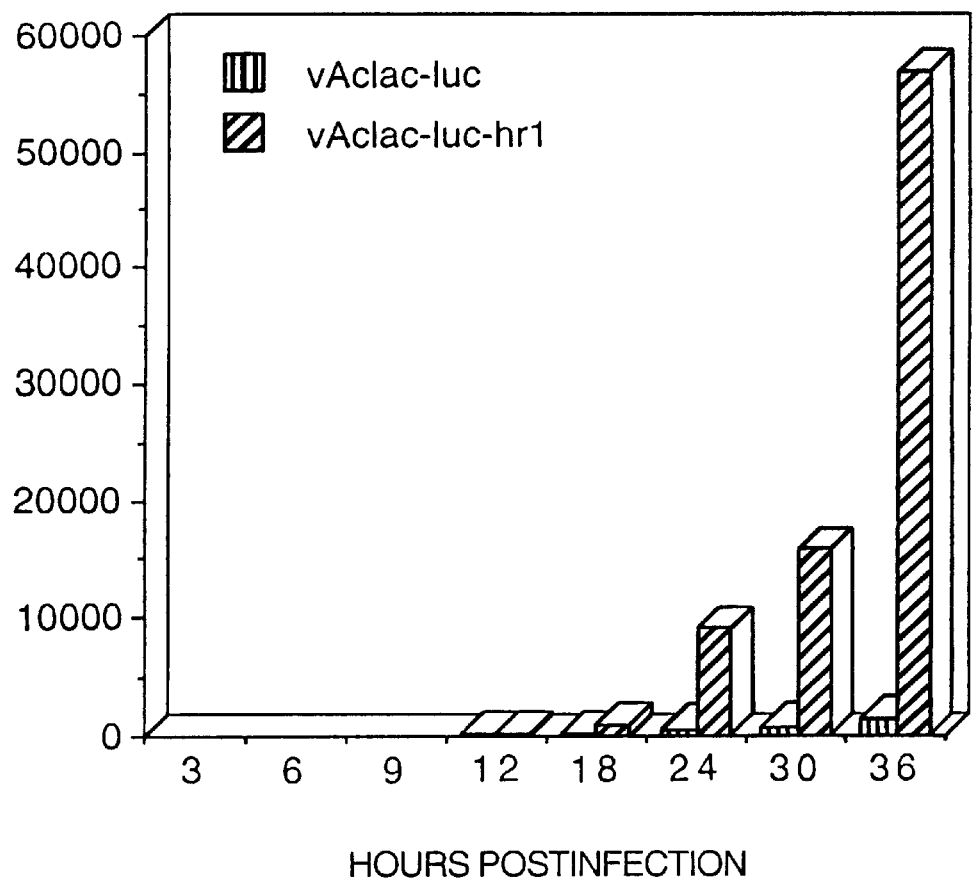
FIG. 5. Depicts the enhancement (35–40 fold) of β-galactosidase reporter expression in insect cells infected with the recombinant baculovirus expression vector carrying an additional copy of hr1 (vAclac-luc-hr11). Mean values of the experiments carried out in duplicates are shown.
Figure 9A:
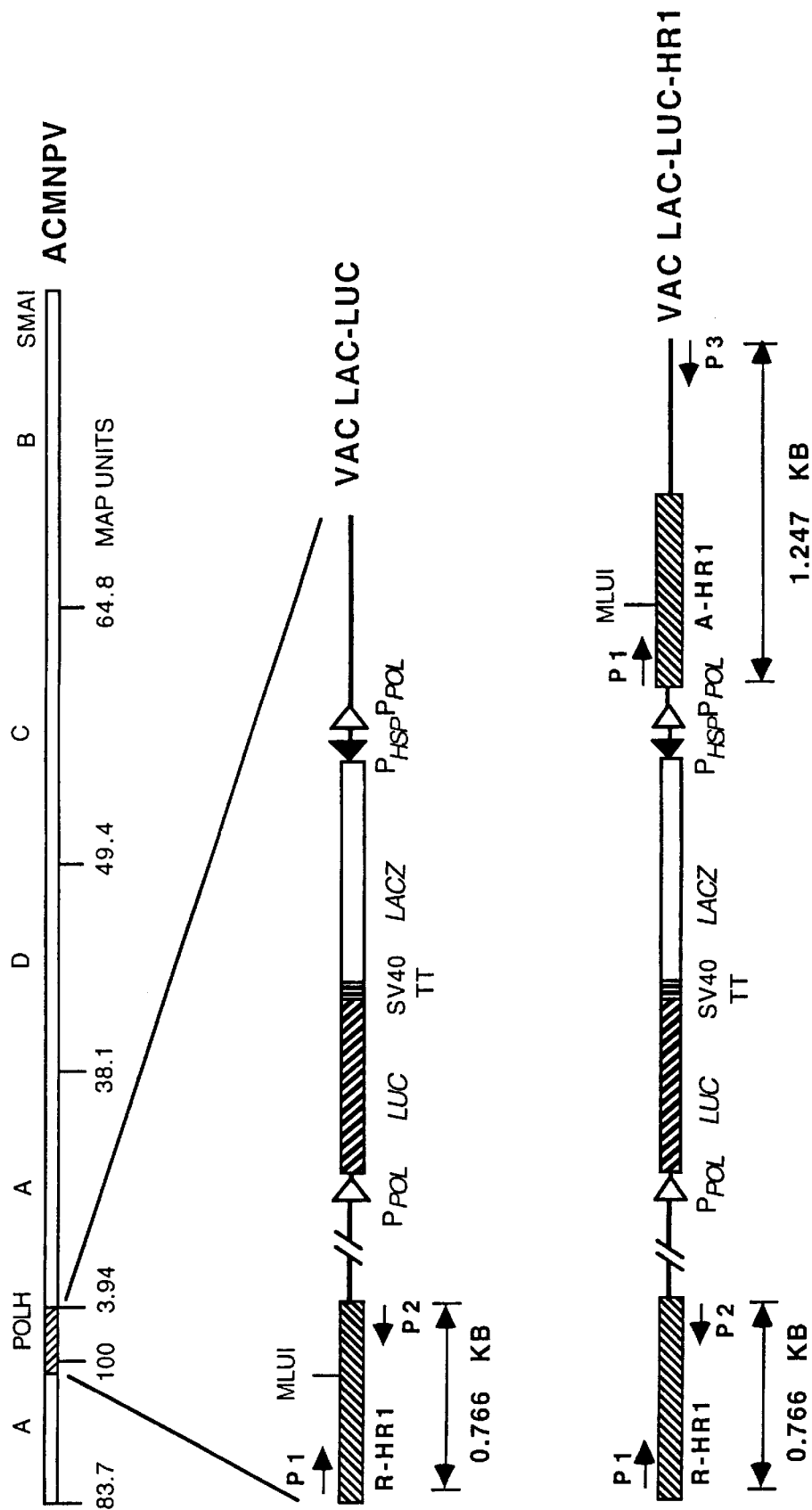
FIG. 9. Illustrates the stability of the recombinant baculovirus expression vector carrying an additional copy of hr1 upto thirty generations by PCR analysis. A: Shows the position of the additional hr1 (a-hr1) in the recombinant baculovirus genome. Primers P1 and P2 amplify the resident copy of the viral hr1 (r-hr1 ) while primers P1 and P3 amplify the additional hr1 sequence (a-hr1). B: PCR amplification profile using the different primers as shown.
Figure 9B:
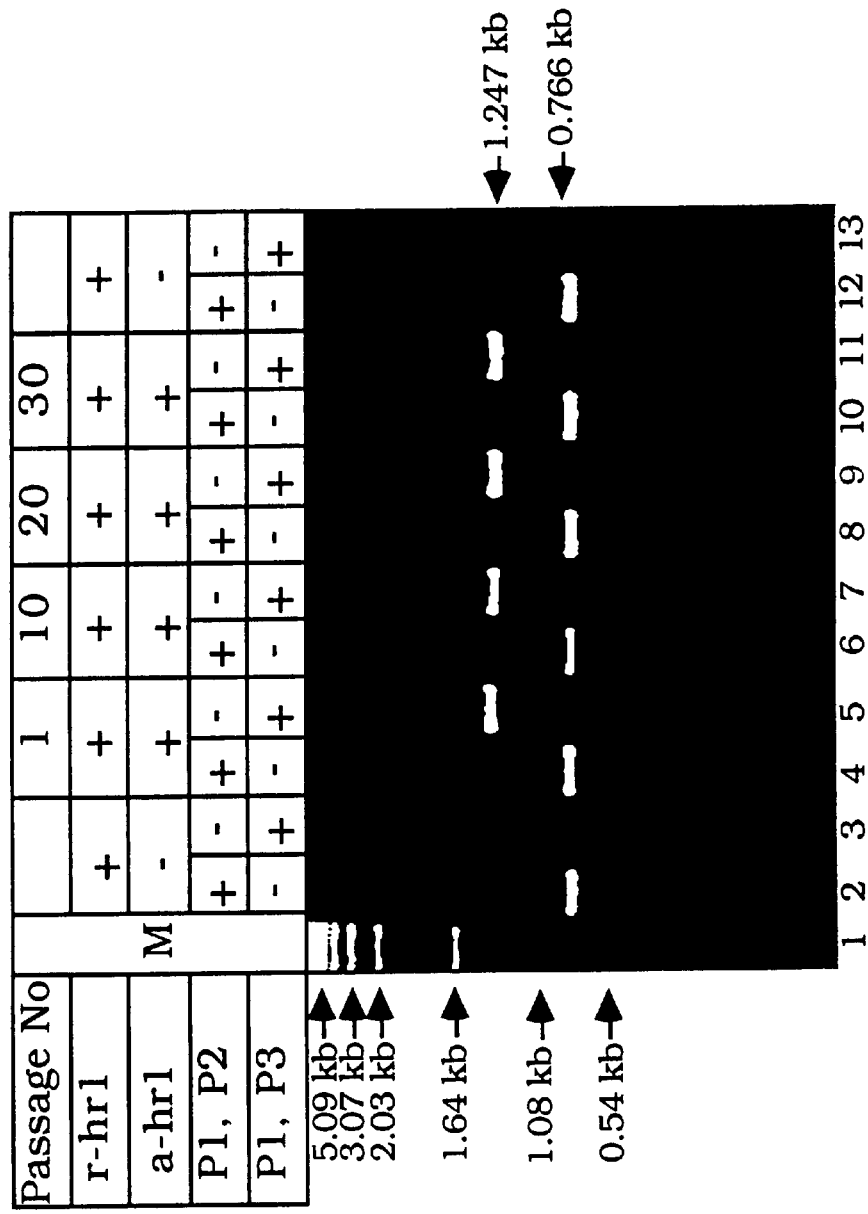

The applicants constructed a recombinant baculovirus vector by standard procedures using the expression vector plasmid pBVlac-luc-hr1. A recombinant virus, vAclac-luc-hr1 carrying an additional hr1 (a-hr1) along with two reporter genes was constructed by co-transfecting pBVlac-luc-hr1 plasmid DNA and linearized baculovirus DNA as per standard methods for constructing recombinant baculovirus which is known to those skilled in this art. vAclac-luc-hr1 has an additional hr1 (a-hr1) along with the luc and lacZ reporter genes (FIG. 9). A recombinant virus (vAclac-luc) that lacks the additional hr1 and only has the resident hr1 (r-hr1) (U. Chatterji et al. Vol. 171, Gene, 209–213, 1996) was used as the control virus in these expression studies. The resident hr1 is located upstream whereas the additional hr1 is placed downstream to the polyhedrin promoter-luciferase reporter cassette. Analyses of reporter gene expression from the recombinant virus vAclac-luc-hr1 and the control virus vAclac-luc showed that the temporal activation profile for the luciferase gene under the polyhedrin promoter followed that expected for a gene under a very late AcMNPV promoter. In the presence of the additional hr1 (a-hr1), enhanced levels of luciferase were observed at all times post infection ( p.i.) with maximum enhancement of about 100-fold, attained at 72 h.p.i. (FIG. 4), over the basal virus vAclac-luc lacking the additional hr1 element. The additional hr1 sequence also enhanced the expression of the β-galactosidase gene under the hsp70 promoter up to 40-fold. Maximum enhancement of lacZ expression was seen between 30 to 36 h.p.i. (FIG. 5). The applicants have thus demonstrated that an additional copy of the hr1 element is capable of exerting its enhancement effect over and above the resident hr1 element. The applicants further demonstrated that an additional copy of the hr1 element is capable of exerting its enhancement effect on the transcription driven by homologous (polyhedrin) promoter and heterologous (hsp 70) promoter.

Figure 6:
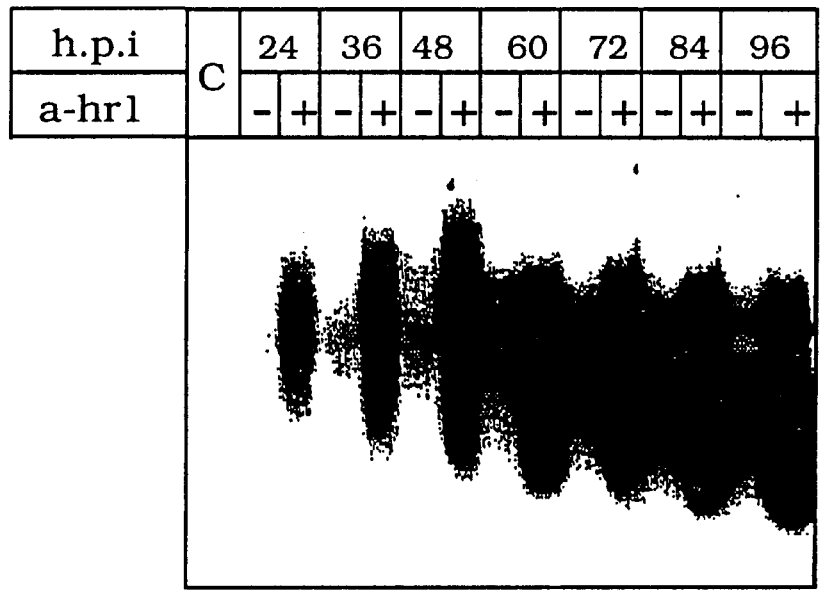
FIG. 6. Depicts RNA levels of the luciferase reporter in insect cells infected with the recombinant baculovirus expression vector, carrying an additional copy of hr1 (vAclac-luc-hr1 ), compared to cells infected with a recombinant baculovirus expression vector with the single resident hr1 element.
Figure 7:
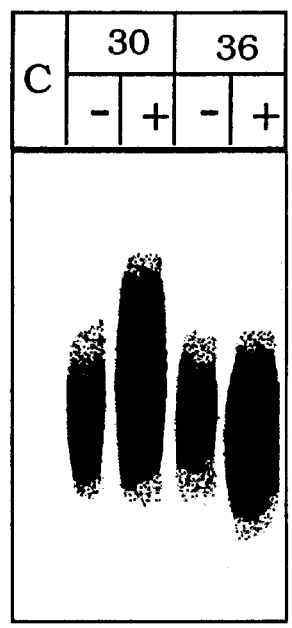
FIG. 7. Depicts RNA levels of the β-galactosidase reporter in insect cells infected with the recombinant baculovirus expression vector, carrying an additional copy of hr1 (vAclac-luc-hr1), compared to cells infected with a recombinant baculovirus with the single resident hr1 element.

The applicants confirmed that elevation of reporter gene expression levels was a direct reflection of enhanced transcription from the two promoters by performing northern blot analysis. Total RNA was isolated from virus infected Sf21 cells using guanidium thiocyanate according to standard procedures (J. Sambrook et al. In: Molecular cloning: A Laboratory Manual, 2nd Ed N.Y.: Cold Spring Harbor Laboratory, 1989). After partial alkaline denaturation followed by overnight transfer carried out in 20×SSC (175.3 g sodium chloride/liter and 88.2 g sodium citrate/liter, pH 7.4), the nylon membrane (Hybond N+) was probed with radiolabeled 1.8 kb luc (FIG. 6) and 3.07 kb lacZ (FIG. 7) fragments separately and autoradiographed. Northern blot analysis compared the relative amounts of RNA produced from cells infected with vAclac-luc and vAclac-luc-hr1 at various time points post infection. A dramatic increase in steady state RNA levels was evident in cells infected with vaclac-luc-hr1 carrying the additional hr1 element. Also, as in the expression profile, maximum increase in luciferase transcript levels was observed at late hours p.i. (FIGS. 6,7).

Enhancement of transcription from the polyhedrin gene promoter in the presence of the additional hr1 sequence was also confirmed by primer extension analysis. Total RNA from cells infected with vAclac-luc and vAc-lac-luc-hr1 was annealed to a $^{32}P$ end-labeled, 20 nt luc-specific primer according to the protocol of J. Sambrook et al (Molecular cloning. A Laboratory Manual, 2nd Edn N.Y.: Cold Spring Harbor Laboratory, 1989). The primer 5'-AAGAATGTAACACAAAGGAA-3' (SEQ ID NO: 1), located 46 nt upstream to the luc initiating ATG, was specific to the 5' end of the luc gene. The annealed mix was precipitated with ethanol and the pellet was resuspended in reverse transcriptase buffer containing RNasin, actinomycin D, dNTPs and AMV reverse transcriptase. The reverse transcription reaction was stopped after 1 hour and the products were precipitated and washed with 70% ethanol. The RNA was then hydrolyzed. The sample was denatured at 75° C. for 5 min after the addition of 4 μl of stop solution from the Sequenase Version 2.0 sequencing kit and fractionated on a sequencing gel. Sequencing of the pSHluc-hrU$_1$DNA was performed using the Sequenase Version 2.0 sequencing kit in the presence of α[$^{35}$S]dATP employing the same primer. The sequencing reaction was run in parallel alongside the primer extension reaction product.

Figure 8:
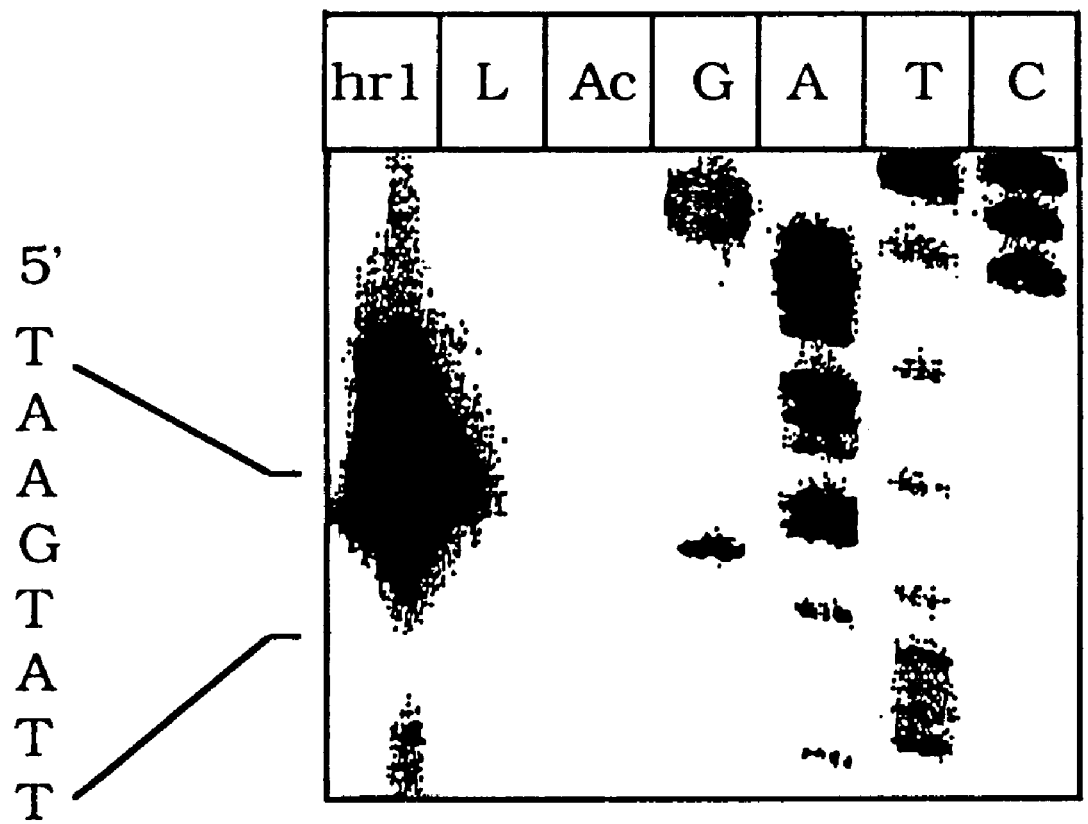
FIG. 8. Illustrates primer extension analysis of luciferase transcripts in vAclac-luc-hr1 infected cells to determine transcription initiation site as well as transcript levels in the presence or absence of the additional hr1. First three lanes represent primer extension analysis from cells infected with vaclac-luc-hr1 (hr1), vAclac-luc (L) and AcMNPV wild type (Ac).

The applicants have determined the site of initiation of transcription of the luciferase gene and confirmed that it represents the authentic polyhedrin transcription start site. Transcriptional enhancement at this authentic initiation site in the presence of the additional hr1 sequence was also evident (FIG. 8).

The Northern blot analyses and primer extension assay together confirm the applicants' claim that the additional hr1 sequence acts as a transcriptional enhancer in infected host cells.

The presence of two identical copies of a DNA sequence in the recombinant viral genome is not a threat to the long term stability of the virus. The applicants studied the stability of their recombinant virus vAclac-luc hr1 that carries two identical copies of the hr1 element. Total cell DNA was isolated from Sf9 cells infected with virus of different passage numbers as described by M. D. Summers & G. E. Smith (A Manual of Methods of Baculovirus Vectors and Insect Cells Culture Procedures. Texas Agricultural Experiment Station Bulletin No. 1555, 1988). For polymerase chain reaction amplification (PCR), primers were designed such that an amplified fragment was generated from the resident hr1 element (r-hr1) and another fragment of a different size was generated from the additional hr1 element (a-hr1) of the recombinant viral genome. The primers used for generating a 0.766 kb fragment from r-hr1 were 5'-TGTTTTACTATCTGTTCT-3' (P1) (SEQ ID NO:2) and 5'-GTTGTCGATAAAACATTC -3', (P2) (SEQ ID NO:3) (FIG. 9). For generating the second 1.247 kb fragment from a-hr1 , the primers used were P1 and 5'-CGATGTTAAATATGTCCAAGC-3' (P3) (SEQ ID NO:4) (FIG. 9). Total DNA (20ng) from different passages of vAclac-luc hr1 and vAclac-luc infected cells was taken in a reaction volume of 25μl containing 10 pmole of each primer, 250 μM each of dATP, dCTP, dGTP and dTTP (Boehringer Mannheim, Germany), 1×Taq polymerase buffer, 0.5 units of Taq polymerase (Genei, India) and 2.5 mM of MgCl$_2$. DNA amplification was carried out for 25 cycles comprising denaturation (2 min. 90° C.), annealing (30 sec, 50° C.), and elongation (1 min, 70° C.), in a Perkin Elmer Cetus Thermal Cycler (PCR, Model 4800). The PCR products were analyzed by electrophoresis on a 1% agarose gel. Specific PCR amplification of the two hr1 sequences was carried out for thirty serial passages of the virus and compared with the amplification products from vaclac-luc. Upon performing PCR in the presence of primers specific for sequences flanking both the hr1 elements, two fragments of the expected sizes were generated from the genomic DNA (FIG. 9) isolated from cells infected with upto 30 passage vAclac-luc-hr1 virus. The applicants have thus demonstrated that the recombinant virus carrying two copies of hr1 is stable at least up to thirty serial passages.

References Cited

| U.S. PATENT DOCUMENTS | | | |
|---|---|---|---|
| 4,745,051 | 5/1988 | Smith and Summers | 435/68 |
| 4,879,236 | 9/1989 | Smith and Summers | 435/235 |
| 5,169,784 | 12/1992 | Summers and Christian | 435/320.1 |

Other Publications

Luckow, V. A. & Summers, M. D. (1988) Trends in the development of baculovirus expression vectors. Biotechnology vol, 6, 47–55. O'Reilly D. R., Miller, L. K. & Luckow, V. A. (1992) Baculovirus expression vectors. A laboratory Mannual (New York: W H Freeman and Co). Summers, M. D. (1987) In: Current communications in molecular biology. Cold Spring Harbor press, TAES Bulletin NO. 1555, 1988.

Cochran, M. A. & Faulkner, P. (1983) Location of homologous DNA sequences interspersed at five regions in the baculovirus AcMNPV genome. J. Virology vol. 45, 961–970.

Kool, M., Voten, J. T. M., Goldbach, R. W., Tramper, J. & Vlak, J. M. (1993) Identification of seven putative origins of Autographa californica multiple nuclear polyhedrosis virus DNA replication. J. General Virology vol. 74, 2662–2668.

Rodems, S. M. and Friesen, P. D. (1995) Transcriptional enhancer activity of hr5 require dual palindrome half sites that mediate binding of a dimeric form of the baculovirus transregulator IE1 J. Virology vol. 69, 5365–5378.

Guarino, L. A., Gonzalez, M. A. & Summers, M. D. (1986) Complete sequence and enhancer function of the homologous DNA regions of Autographa californica nuclear polyhedrosis virus. J. Virology vol. 60, 224–229.

Guarino, L. A. & Summers, M. D. (1986) Interspersed homologous DNA of Autographa californica nuclear polyhedrosis virus enhances delayed- early gene expression. J. Virology vol. 60, 215–223.

Liu. A., Qin, J., Rankin, C., Hardin, S. E. & Weaver, R. F. (1986) Nucleotide sequence of a portion of the Autographic californica nuclear polyhedrosis virus genome containing the EcoRI site-rich region (hr5) and open reading frame just 5' of the p10 (gene. J. General Virology vol. 67, 2565–2570.

Pearson, M., Bjormson, R., Pearson, G. and Rohrmann, G. (1992) The Autographa californica baculovirus genome: evidence for multiple replication origins. Science vol. 257-1382–1384.

Kool, M., Van Den Berg, P. M. M. M., Tramper, J., Goldbach, R. V. & Vlak, J. M. (1993) Location of two putative origins of DNA replication of Autographa californica nuclear polyhedrosis virus. Virology vol. 192,94–101.

Kool, M., Voeten, J. J. M., Goldbach, R. W. & Vlak, J. M. (1994) Functional mapping of regions of the Autographa californica nuclear polyhedrosis viral genome required for DNA replication. Virology vol. 198, 680–689.

Ahrens, C. H., Leisy, D. J. & Rohrmann, G. F. (1995) Baculovirus DNA replication. In DePamphilis, M. (ed.) DNA replication in eukaryotes.

Kool, M., Ahrens, C. H., Vlak, J. M. & Rohrmann, G. F. (1995) Replication of baculovirus DNA. J. General Virology vol. 76, 2103–2118.

Leisy, D. J. & Rohrmann, G. F. (1993) Characterization of the replication of plasmids containing hr sequences in baculovirus-infected Spodoptera frugiperda cells. Virology vol. 196, 722–730.

Carson, D. D., Summers, M. D. & Guarino, L. A. (1991) Transient expression of the Autographa californica nuclear polyhedrosis virus immediate-early gene, IE-N is regulated by three viral elements. J. Virology vol. 65, 945–951.

Lu, A. & Carstens, E. B. (1993) Immediate-early baculovirus genes transactivate the p13 promoters of Autographa californica nuclear polyhedrosis virus. Virology vol. 193, 710–718.

Nissen, M. S. & Friesen, P. D. (1989) Molecular analysis of the transcriptional regulatory region of an early baculovirus gene. J. Virology vol. 63, 493–503.

Rodems, S. M. & Friesen, P. D. (1993) The hr5 transcriptional enhancer stimulates expression from the Autographa californica nuclear polyhedrosis virus genome but is not required for virus replication. J. Virology vol. 67, 5776–5785.

Guarino, L. A. & Dong, W. (1991) Expression of an enhancer-binding protein in insect cells transfected with the Autographa californica nuclear polyhedrosis virus IE-I gene. J. Virology vol. 65, 3676–3680.

Guarino, L. A. & Dong, W. (1994) Functional dissection of the Autographa californica nuclear polyhedrosis virus enhancer element hr5. Virology vol. 200, 328–335.

Habib, S., Pandey, S., Chatterji, J., Burman, S., Ahmad, R., Jain, A. & Hasnain, S. E. (1996) Bifunctionality of the homologous region sequence (hr1 ): Enhancer and ori functions have different sequence requirements. DNA Cell Biology vol. 15, 737–747.

Israel, D. I. & Kaufman, R. J. (1989) Highly inducible expression from vectors containing multiple GRE's in CHO cells overexpressing the glucocorticoid receptor. Nucleic Acid Research vol. 17, 4589–4604.

Hink, W. F. (1970) Established insect cell line from the cabbage looper, Trichoplusia ni. Nature col. 226, 466–467.

Webb & Summers, (1990) A J. Methods in Cell and Molec. Biol. vol. 2, 173–188, Chatterji, U. Ahmad, R., Venkaiah, B. and Hasnain, S. E. (1996) A recombination-efficient baculovirus vector for simultaneous expression of multiple genes. Gene, vol. 171, 209–213.

Miller, J. H. (1992) A short course in bacterial Genetics. A laboratory manual and Handbook for Escherichia coli and related bacteria. CSHL Press, Cold Spring Harbor, N.Y.

Pennock, G. D., Shoemaker, C. & Miller, L. K. (1984) Strong and regulated expression of Escherichia coli β-galactosidase in insect cells with a baculovirus vector. Mol. Cell Biol. vol. 4, 399–406.

Sambrook, J., Fritsch, E. F. & Maniatis, T. (1989) Molecular cloning: A Laboratory Manual, 2nd Edn New York: Cold Spring Harbor Laboratory.

We claim:

1. A method for enhancing foreign gene expression in a baculovirus expression vector system comprising infecting an insect cell with a baculovirus viral expression vector comprising two copies of enhancer sequence hr1, at least one promoter and at least one foreign gene and culturing the cell under conditions whereby the protein encoded by the foreign gene is expressed.

2. The method of claim 1 wherein the promoter is a homologous promoter.

3. The method of claim 1 wherein the promoter is a heterologous promoter.

4. The method of claim 1 wherein the promoter is a polyhedrin promoter.

5. The method of claim 1 wherein the promoter is a Drosophila hsp 70 promoter.

6. The method of claim 1 wherein the vector comprises two promoters said promoters being two homologous promoters, two heterologous promoters or a homologous promoter and a heterologous promoter.

7. The method of claim 1 wherein the vector comprises two promoters said promoters being two polyhedrin promoters, two Drosophila hsp 70 promoters or a polyhedrin promoter and a Drosophila hsp 70 promoter.

8. The method of claim 1 wherein two or more promoters are present in the vector.

9. The method of claim 1 wherein the foreign gene codes for the protein luciferase.

10. The method of claim 1 wherein the gene codes for the protein β-galactosidase.

11. The method of claim 1 wherein at least two foreign genes are present in the vector.

12. The method of claim 1 wherein at least three foreign genes are present in the vector.

13. The method of claim 12 wherein one foreign gene codes for the protein luciferase and another foreign gene codes for β-galactosidase.

14. The method of claim 1 wherein foreign gene expression is enhanced 40–100 fold.

15. A method for transiently enhancing foreign gene expression using a baculovirus expression vector system comprising infecting an insect cell with wild type baculovirus and a viral expression plasmid comprising two copies of enhancer sequence hr1, at least one promoter and at least one foreign gene and culturing the cell under conditions whereby the protein encoded by the foreign gene is expressed.

16. The method of claim 15 wherein the promoter is a polyhedrin promoter.

17. The method of claim 15 wherein the promoter is a Drosophila hsp 70 promoter.

18. The method of claim 15 wherein the plasmid comprises two promoters said promoters being two polyhedrin promoters, two Drosophila hsp 70 promoters or a polyhedrin promoter and a Drosophila hsp 70 promoter.

19. The method of claim 15 wherein at least two foreign genes are present in the plasmid.

20. The method of claim 15 wherein at least three foreign genes are present in the plasmid.

21. The method of claim 15 wherein foreign gene expression is enhanced 12–18 fold.

22. A recombinant expression plasmid comprising two enhancer sequences hr1, at least one promoter and at least one foreign gene.

23. The recombinant expression plasmid of claim 22 wherein the promoter is a polyhedrin hsp 70 promoter.

24. The recombinant plasmid of claim 22 wherein the promoter is a Drosophila hsp 70 promoter.

25. The recombinant expression plasmid of claim 22 wherein the plasmid comprises two promoters said promoters being two polyhedrin promoters, two Drosophila hsp 70 promoters or a polyhedrin promoter and a Drosophila hsp 70 promoter.

26. The recombinant expression plasmid of claim 22 wherein at least two foreign genes are present in the plasmid.

27. The recombinant expression plasmid of claim 22 wherein at least three foreign genes are present in the plasmid.

28. A recombinant baculovirus vector comprising DNA of the plasmid of claim 22.

29. An insect cell comprising the plasmid of claim 22.

30. A recombinant baculovirus vector comprising DNA of the plasmid of claim 23.

31. A recombinant baculovirus vector comprising DNA of the plasmid of claim 24.

32. A recombinant baculovirus vector comprising DNA of the plasmid of claim 25.

33. A recombinant baculovirus vector comprising DNA of the plasmid of claim 26.

34. A recombinant baculovirus vector comprising DNA of the plasmid of claim 27.

35. The recombinant baculovirus vector of claim 28 stable up to 30 passages.

36. The recombinant baculovirus vector of claim 30 stable up to 30 passages.

37. The recombinant baculovirus vector of claim 31 stable up to 30 passages.

38. The recombinant baculovirus vector of claim 32 stable up to 30 passages.

39. The recombinant baculovirus vector of claim 33 stable up to 30 passages.

40. The recombinant baculovirus vector of claim 34 stable up to 30 passages.

41. An insect cell comprising the plasmid of claim 23.
42. An insect cell comprising the plasmid of claim 24.
43. An insect cell comprising the plasmid of claim 25.
44. An insect cell comprising the plasmid of claim 26.
45. An insect cell comprising the plasmid of claim 27.
46. An insect cell comprising the vector of claim 28.
47. An insect cell comprising the vector of claim 30.
48. An insect cell comprising the vector of claim 31.
49. An insect cell comprising the vector of claim 32.
50. An insect cell comprising the vector of claim 33.
51. An insect cell comprising the vector of claim 34.

* * * * *